(12) United States Patent
Peyman

(10) Patent No.: US 7,083,802 B2
(45) Date of Patent: Aug. 1, 2006

(54) TREATMENT OF OCULAR DISEASE

(75) Inventor: Gholam Peyman, New Orleans, LA (US)

(73) Assignee: Advanced Ocular Systems Limited, Nedlands (AU)

( * ) Notice: Subject to any disclaimer, the term of this patent is extended or adjusted under 35 U.S.C. 154(b) by 202 days.

(21) Appl. No.: 10/631,143

(22) Filed: Jul. 31, 2003

(65) Prior Publication Data

US 2005/0025810 A1    Feb. 3, 2005

(51) Int. Cl.
*A61F 13/00* (2006.01)
*A61F 2/00* (2006.01)
*A61K 9/00* (2006.01)

(52) U.S. Cl. .................. 424/422; 424/400; 424/427; 424/428

(58) Field of Classification Search ............. 424/400, 424/422, 423, 427, 428
See application file for complete search history.

(56) References Cited

U.S. PATENT DOCUMENTS

| | | | |
|---|---|---|---|
| 4,079,038 A | 3/1978 | Choi et al. ............. 260/47 |
| 4,093,709 A | 6/1978 | Choi et al. ............. 424/19 |
| 4,131,648 A | 12/1978 | Choi et al. ............. 424/22 |
| 4,138,344 A | 2/1979 | Choi et al. ............. 252/1 |
| 4,180,646 A | 12/1979 | Choi et al. ............. 528/153 |
| 4,304,767 A | 12/1981 | Heller et al. ............. 424/78 |
| 4,946,931 A | 8/1990 | Heller et al. ............. 528/320 |
| 5,294,604 A | 3/1994 | Nussenblatt et al. ............. 514/11 |
| 5,387,589 A * | 2/1995 | Kulkarni |
| 5,411,952 A | 5/1995 | Kaswan |
| 5,457,182 A | 10/1995 | Wiederrecht et al. ............. 530/402 |
| 5,770,607 A | 6/1998 | Honbo et al. ............. 514/302 |
| 5,773,019 A | 6/1998 | Ashton et al. ............. 424/423 |
| 5,952,371 A | 9/1999 | Baker et al. ............. 514/443 |
| 5,968,543 A | 10/1999 | Heller et al. ............. 424/425 |
| 6,004,565 A | 12/1999 | Chiba et al. ............. 424/278.1 |
| 6,179,817 B1 | 1/2001 | Zhong ............. 604/265 |
| 6,238,799 B1 | 5/2001 | Opolski ............. 428/423 |
| 6,239,113 B1 | 5/2001 | Dawson et al. ............. 514/29 |
| 6,258,856 B1 | 7/2001 | Chamberlain et al. ............. 514/912 |
| 6,306,422 B1 | 10/2001 | Batich et al. ............. 424/423 |
| 6,331,313 B1 * | 12/2001 | Wong et al. |
| 6,350,442 B1 | 2/2002 | Garst ............. 424/78.04 |
| 6,413,536 B1 | 7/2002 | Gibson et al. ............. 424/423 |
| 6,436,906 B1 | 8/2002 | Or et al. ............. 514/29 |
| 6,440,942 B1 | 8/2002 | Or et al. ............. 514/30 |
| 6,462,026 B1 | 10/2002 | Or et al. ............. 514/30 |
| 6,462,071 B1 | 10/2002 | Castillejos |
| 6,482,799 B1 | 11/2002 | Tuse et al. |
| 6,489,335 B1 | 12/2002 | Peyman ............. 514/291 |
| 6,534,693 B1 | 3/2003 | Fischell et al. |
| 6,596,296 B1 | 7/2003 | Nelson et al. ............. 424/425 |
| 6,613,355 B1 | 9/2003 | Ng et al. ............. 424/462 |
| 6,617,345 B1 | 9/2003 | Gregory et al. ............. 514/395 |
| 6,667,371 B1 | 12/2003 | Ng et al. ............. 525/462 |
| 6,670,398 B1 | 12/2003 | Edwards et al. |
| 6,673,807 B1 | 1/2004 | Sakai et al. |
| 6,713,081 B1 * | 3/2004 | Robinson et al. |
| 6,864,232 B1 | 3/2005 | Ueno ............. 514/9 |
| 6,872,383 B1 * | 3/2005 | Ueno |
| 2002/0015957 A1 | 2/2002 | Hageman et al. |
| 2002/0187998 A1 | 12/2002 | Ueno |
| 2003/0044452 A1 | 3/2003 | Ueno |
| 2003/0069232 A1 | 4/2003 | Chiou |
| 2004/0092435 A1 | 5/2004 | Peyman |
| 2004/0198763 A1 | 10/2004 | Ueno |
| 2005/0025810 A1 | 2/2005 | Peyman |
| 2005/0063996 A1 | 3/2005 | Peyman |
| 2005/0063997 A1 | 3/2005 | Peyman |
| 2005/0064010 A1 | 3/2005 | Cooper et al. |
| 2005/0070468 A1 | 3/2005 | Ueno |

FOREIGN PATENT DOCUMENTS

| | | |
|---|---|---|
| AU | 17386/88 | 3/1991 |
| AU | 20350/92 | 1/1993 |
| CN | 1333018 | 1/2002 |
| CN | 1340358 | 3/2003 |
| CN | 1456350 | 11/2003 |
| DE | 19810655 | 9/1999 |
| EP | 0532862 | 3/1993 |
| EP | 1074255 | 2/2001 |

(Continued)

OTHER PUBLICATIONS

Apel, Andrew et al., *A sybconjunctival degradable implant for cyclosporine delivery in corneal transplant therapy*, Curr. Eye Res. 14:659-667 1995.

(Continued)

*Primary Examiner*—Humera N. Sheikh
(74) *Attorney, Agent, or Firm*—Frommer Lawrence & Haug LLP; Thomas J. Kowalski

(57) ABSTRACT

A formulation to treat ocular conditions such as dry eye disease, as well as other conditions, is disclosed. Rapamycin and/or ascomycin is administered intraocularly, such as by topical application, injection into the eye, or implantation in or on the eye. For example, a topical administration may contain between about 50 pg/ml drug to about 50 μg/ml drug in a formulation which may be applied at bedtime or throughout the day. For injection, a dose of about 50 pg/ml to about 200 μg/ml may be used. Rapamycin and/or ascomycin may also be administered in milligram quantities as a surgical implant, for example, in a diffusible walled reservoir sutured to the wall of the sclera, or may be contained within an inert carrier such as microspheres or liposomes to provide a slow-release drug delivery system.

11 Claims, No Drawings

FOREIGN PATENT DOCUMENTS

| | | |
|---|---|---|
| EP | 1142566 | 10/2001 |
| JP | 07010752 | 1/1995 |
| JP | 1997030966 | 2/1997 |
| JP | 09315954 | 12/1997 |
| JP | 10218787 | 8/1998 |
| JP | 2001064198 | 3/2001 |
| WO | WO 89/01772 | 3/1989 |
| WO | WO 99/22722 | 5/1999 |
| WO | WO 99/34830 | 7/1999 |
| WO | WO 99/42104 | 8/1999 |
| WO | WO 00/66122 | 11/2000 |
| WO | WO 02/24234 | 3/2002 |
| WO | WO 03/017990 | 3/2003 |
| WO | WO 03/051385 | 6/2003 |
| WO | WO 2004/014373 | 2/2004 |
| WO | WO 2004/027027 | 4/2004 |
| WO | WO 2004/043480 | 5/2004 |
| WO | WO 2004/096261 | 11/2004 |
| WO | WO 2005/011813 | 2/2005 |
| WO | WO 2005/027906 | 3/2005 |
| WO | WO 2005/030205 | 4/2005 |

OTHER PUBLICATIONS

PCT, *International Search Report*, for PCT/2004/024054, filed Jul. 27, 2004, 7 pg.

U.S. Appl. No. 10/187,013, filed Jul. 2, 2002, Ueno, *Composition for Topical Administration*, published Mar. 5, 2003.

U.S. Appl. No. 10/247,220, filed Sep. 19, 2002, Peyman, *Treatment of Ocular Disease*, published Jan. 23 2003.

U.S. Appl. No. 10/354,083, filed Jan. 30, 2003, Ueno, *Use of Macrolide Compounds for the Treatment of Dry Eye*, published Jul. 10, 2003.

Goodman & Gilman, Eds., *The Pharmacological Basis of Therapeutics*, 8th Edition, Pergamon Press, New York, 1990, pp. 1024-1033.

Peyman et al., Eds., *Vitreoretinal Surgical Techniques*, (Martin Dunitz, London, 2001, Chapter 45, pp. 521-531.

Wise, Ed., *Handbook of Pharmaceutical Controlled Release Technology*, Marcel Dekker, New York, 2000, pp. 108-119, 155-209, 271-285, 510-516.

Algvere et al., *Long-term outcome of RPE allografts in non-immunosuppressed patients with AMD*, European J of Ophthalmology (1999) 9(3):217-230.

Anderson et al., *A Role for Local Inflammation in the Formation of Drusen in the Aging Eye*, American Journal of Ophthalmology, vol. 134, No. 3, Sep. 2002,. pp. 411-413.

Aramant et al., *Retinal transplanatation*, Science & Medicines (2000), 7:20-29.

Aron-Rosa, *Pulsed Nd:YAG lasers in ophthalmology*, Nd:YAG Laser Applications pp. 34-48, 1986.

Carmo et al., *Effect of cyclosporin A on the blood-retinal barrier permeability in streptozotrocin-induced diabetes*, Mediators of Inflammation (2000), 9(5):243-248.

Cicciarell et al., *Pharmacokinetics of subconjunctivally administered cylcosporine A. Local delivery prior to chemotherapy for retinoblastoma*, IOVS (Mar. 15, 2001), 42(4):S332.

Costantini, LC, et al., *Immunophilin Ligands and GDNF Enhance Neurite Branching or Elongation from Developing Dopamine Neurons in Culture*, Experimental Neurology 164,60-70 (2000).

Das et al., *The transplantation of human fetal neuroretinal cells in advanced retinitis pigmentosa patients: Results of a long-term safety study*, Experimental Neurology (1999), 157:58-68.

Del Cerro et al., *Histologic correlation of human neural retinal transplantation*, Invest. Ophthalmology & Visual Science (2000) 41(10): 3142-3148.

Dewey, *2003 PCO Update: Part 1—How the square-edged IOL prevents posterior capsular opacification*, Cataract & Refractive Surgery Today, Sep. 2003, pp. 20-22.

Donnenfeld et al., *Cyclosporine provides effective treatment for dry eye*, Therapeutic Updates In Ophthalmology, Special Issue, Jul. 1999, pp. 1-3.

Eneydi et al., *Pharmacokinetics and toxicity of an intravitreal device providing sustained release of cyclosporine (CsA) and dexamethasone (DEX)*, Investigative Ophthalmology and Visual Science, vol. 35, No. 4, 1994, p. 1906, and Annual Meeting of the association for Research in Vision and Ophthalmology, Sarasota, FL, USA, May 1-6, 1994 abstract.

Enyedi et al., *An intravitreal device providing sustained release of cyclosporine and dexamethasone*, Current Eye Research, May 1996, vol. 15, No. 5, pp. 549-557.

Garweg et al., *Therapy of Goldmann-Favre's Vitreo-Retinal Degeneration with Cyclosporin A and Bromocriptine*, Klinische Monatsblatter fur Augenheilkunde, vol. 199, No. 3, Sep. 1991, pp. 199-205.

Gilbard, *EW Interview: Electrolyte balance is key to dry-eye product's success*, EyeWorld, Feb. 1999, pp. 20ff.

Grisolano et al., *Retinal Toxicity Study of Intravitreal Cyclosporin*, Opthalmic Surgery, Mar. 1986, 17:155-156.

Jiang et al, *Corneal electroretinographic function rescued by normal retinal pigment epithelial grafts in retinal degenerative Royal College of Surgeons rats*, Invest. Ophthalmology & Visual Science (1994). 35)13):4300-4308.

Karacortu et al, *Lack of toxicity of intravitreally administered interferon Alpha-2a*, Ophthalmic Surgery (1999) 23:833-835.

Keep et al, *Introduction: Immunosuppressants as Neuroprotective Agents, Immunosuppressant Analogs in Neuroprotection, Part I: Immunosuppressants, Neurologic Disorders, and Neuroprotection*, Ed. Borlongan & Sanberg, Humana Press Inc., Totowa NJ, pp. 3-32, Nov. 2002.

Kiryu et al., *In Vivo Evaluation of the Inhibitory Effects of Tacrolimus (FK506) on Leukocyte Accumulation During Retinal Ischemia Reperfusion Injury*, Poster Presentation 1247-B128, Mar. 1998.

Lai et al, *Local Immunosuppression prolongs survival of RPE xenografts labeled by retroviral gene transfer*, IOVS (Sep. 2000) 41(10):3134-3141.

Lallemand et al., *Cyclosporine A delivery to the eye: A pharmaceutical challenge*, European Journal of Pharmaceutics and Biopharmaceutics, 56 (2003), pp. 307-318.

Lipner, *Dry Eye 101: Developing etiologies and treatmetns for this widespread syndrome*, EyeWorld, Feb. 1999, pp. 19ff.

Lipper et al., *Recent therapeutic advances in dermatology*, JAMA, vol. 283, No. 2, Jan. 12, 2000, pp. 175-177.

Lopez et al., *Transplanted retinal pigment epithelium modifies the retinal degeneration in the RCS*, Invest. Ophthalmology & Visual Science (1989), 30:586-588.

Lund, et al., *Subretinal transplantation of genetically modified human cell lines attenuates loss of visual function in dystrophic rats*, PNCS (2001), 98(17): 9942-9947.

Martin DF et al., *Synergistic Effect of Rapamycin and Cyclosporin A in the Treatment of Experimental Autoimmune Uveoretinits*, The Journal of Immunology, 1995, 154:922-927.

Nicoletti et al., *The Effects of deoxyspergualin on the development of diabetes in diabetes-prone BB rats*, Scandinavian Journal of Immunology (1992) 36(3):415-420.

Passos et al, *Ocular Toxicity of Intravitreal Tacrolimus*, Ophthalmic Surgery and Lasers, Mar./Apr. 2002, vol. 22, No. 2, pp. 140-144.

PCT, *International Search Report*, PCT/US03/28315, mailed Jun. 15, 2004, 6 pages.

Peyman et al., *Intravitreal Surgery*, Principles and Practice, 2nd Edition, 1994, Ppleton & Lange, Connecticut, pp. 443-452.

Peyman et al., *Keratitis (Noninfectious)*, Principles and Practice of Ophthalmology, W.B. Saunders Company, 1980, pp. 446-449.

Peyman et al., *Intravitreal drug therapy*, Japanese Journal of Ophthalmology (1989), 33(4): 392-404.

Peyman, *Pupillary Membranes: Nd'YAG Capsulotomy*, Intravitreal Surgery, Norwalk CT, Appleton & Lange, 1994, pp. 253-257.

Peyman et al., *Implantation of a sustained-release ganciclovir implant*, Vitreoretinal Surgical Techniques, Martin Dunitz Ltd., 2001, Chapter 45, pp. 521-531.

Schonfield and Kirst, *Macrolide Antibiotics*, Birkhausen, Basil, Switzerland, 2002, pp. 1-36.

Shen et al., *Combined effect of cyclosporine and sirolimus on improving the longevity of recombinant adenovirus-mediated transgene expression in the retina*, Archives of Ophthalmology (Jul. 2001), 119(7): 1033-1043.

Stosic-Grujicic et al, *Leflunomide protects mice from multiple low dose streptozotocin (MLD-SA)-induced insulitis and diabetes*, Clinical & Experimental Immunology (1999) 117(1):44-50.

Wakelee-Lynch, *Interferon may offer first drug therapy for diabetic retinopathy*, Diabetes Care (1992), 15(2):300-301.

Wise, *Handbook of Pharmaceutical Controlled Release Technology*, Marcel Dekker, New York, 2000.

* cited by examiner

TREATMENT OF OCULAR DISEASE

FIELD OF THE INVENTION

The invention is directed to the use of rapamycin and ascomycin for therapeutic treatment of ocular conditions, including dry eye disease.

BACKGROUND

Dry eye disease encompasses any condition where the tear film loses water and becomes more concentrated. It is a common complaint, affecting three million people in the United States alone, yet it is difficult to diagnose and treat. The loss of water from the tear film causes a corresponding rise in tear osmolarity. The increased osmolarity results in symptoms such as a sandy-gritty feeling in the eye, burning, irritation, or a foreign-body sensation that worsens during the day. Patients suffering from dry eye disease complain of mild to severe symptoms, with signs ranging from minimal superficial punctate keratitis to corneal perforation.

Dry eye disease has a chronic remitting and relapsing nature and may result from a number of factors. The disease may be a natural part of the aging process, affecting 15%–20% of adults over age 40. It may also result from pathological processes such as diseases of the lacrimal glands, mucus glands, and/or lipid producing glands, and may occur with cell infiltration or atrophy of the lacrimal gland (Sjögren's syndrome). Estrogen deficiency in postmenopausal women is also postulated to result in dry eye disease.

One method to treat dry eye disease is by topical administration of over-the-counter drugs that serve as artificial tears. Numerous varieties of these artificial tears are available (TheraTears® (Advanced Vision Research), Refresh® and Celluvisce® (Allergan), Tears Natural® and Bion Tears® (Alcon), GenTeal® and HypoTears® (CIBA Vision), each of which contain electrolytes and has varying pH levels, osmolarities, and surface tensions. Another method to treat dry eye disease is by surgery to close the lacrimal drainage ducts using punctum plugs. Neither method, however, is completely desirable. Artificial tears do not have a constant flow rate as do human tears, and treat the symptoms rather the cause of the disease. Surgery has its attendant risks, and may not be a viable option in older patients.

It is known that Cyclosporin A (cyclosporine, Allergan Inc.), may treat dry eye disease because patients administered Cyclosporin A for other disorders have shown a marked increase in tear flow. A topical formulation containing Cyclosporin A (Arrestase®, Allergan Inc.) is currently under review by the Food and Drug Administration. Cyclosporin A is an immunomodulator, suggesting that immune-mediated inflammation contributes to dry eye disease. Cyclosporin A has been used to treat various ocular pathologies such as glaucoma, corticosteroid-induced ocular hypertension, allograft rejection, infections, and ocular surface disease. It is also known that Cyclosporin A may be used in the eye to treat uveitis (inflammation of the uvea) by topical, intravitreal or systemic administration. Doses of 0.05%, 0.1%, and 0.5% Cyclosporin A have been reported. Cyclosporin A has good penetration into the cornea but not into the anterior chamber, and does not increase intraocular pressure or cause cataracts.

Tacrolimus (Prograf®, previously known as FK-506) is an immunomodulating drug that has been applied topically to treat a variety of dermatoses. Topical administration of tacrolimus at doses ranging from 0.03%–0.3% resulted in significant clinical improvement in atopic dermatitis after 2–3 weeks treatment, and tacrolimus treatment of other dermatologic diseases shows promise. Tacrolimus, like cyclosporine, blocks the signal transduction pathway needed to induce interleukin-2 gene expression and thereby activate T lymphocytes. In addition to suppressing T cell activation, tacrolimus inhibits anti-IgE-triggered histamine release and inhibits prostaglandin D2 synthesis in human skin mast cells. While oral administration produces limiting adverse effects (systemic immunosuppression, infection, neural toxicity, nephrotoxicity, and hypertension), topical administration for treatment of dermatoses at concentrations up to 0.3% showed no significant difference in effects between treated and control groups. In addition, tacrolimus is well tolerated locally and only occasionally causes mild irritation. The use of tacrolimus to treat a variety of ocular conditions, including dry eye disease, has been reported in U.S. Pat. No. 6,489,335.

Other compositions and methods to treat ocular conditions and enhance ocular lubrication would be desirable.

SUMMARY OF THE INVENTION

A method to treat an ocular condition in a patient by intraocularly administering a pharmaceutically acceptable formulation of rapamycin in an amount effective to treat the condition. The method provides treatment while avoiding systemic administration of rapamycin. In one embodiment, a sustained release pharmaceutically acceptable formulation is implanted intraocularly. For example, a matrix containing in the range of between about 3 mg rapamycin to about 5 mg rapamycin may be implanted in or on the eye and may continuously deliver rapamycin for ten or more years. In another embodiment a concentration up to about 200 µg rapamycin is administered intraocularly without substantial toxicity. In another embodiment, rapamycin at a concentration in the range of about 1 ng/ml (0.0000001%) to less than 0.1 µg/mi (less than 0.001%) is administered topically. In other embodiments, rapamycin at a concentration in the range of about 1 ng/ml to about 200 µg/ml is injected under the conjunctiva, or a concentration in the range of about 1 ng/0.1 ml to about 200 µg/ml is injected in the vitreous, or a concentration in the range of about 20 µg/ml to about 200 µg/ml is injected behind the eyeball.

The method may prevent, decrease the time of onset, or lessen the severity of a wide variety of ocular conditions such as retinitis pigmentosa, ocular irritation following corneal surgery (e.g., LASIK surgery), age related macular degeneration, diabetic retinopathy, dry eye disease, scleritis, papillitis, and uveitis, as examples. Rapamycin may be administered in combination with Cyclosporin A and/or tacrolimus for intraocular administration without toxicity-limiting effects. Rapamycin may also be administered in combination with antibiotics without toxicity-limiting effects.

Another embodiment of the invention is a method to treat ocular conditions including ocular irritation following corneal surgery, retinitis pigmentosa, age related macular degeneration, diabetic retinopathy, scleritis, papillitis, and uveitis by intraocular administration of ascomycin. Ascomycin may be the sole active agent or, alternatively, it may be administered in combination with other agents, including but not limited to rapamycin, Cyclosporin A, tacrolimus, and antibiotics.

In one embodiment, a sustained release pharmaceutically acceptable formulation is implanted intraocularly. For example, a matrix containing in the range of between about 3 mg ascomycin to about 5 mg ascomycin may be implanted in or on the eye and may continuously deliver ascomycin for ten or more years. In another embodiment a concentration up to about 200 μg ascomycin is administered intraocularly without substantial toxicity. In another embodiment, ascomycin at a concentration in the range of about 1 ng/ml (0.0000001%) to less than 1 μg/ml (less than 0.0001%) is administered topically. In other embodiments, ascomycin at a concentration in the range of about 1 ng/ml to about 200 μg/ml is injected under the conjunctiva, or a concentration in the range of about 1 ng/0.1 ml to about 200 μg/ml is injected in the vitreous, or a concentration in the range of about 20 μg/ml to about 200 μg/ml is injected behind the eyeball.

The invention also encompasses a composition formulated for intraocular administration and dosing with rapamycin and/or ascomycin in a pharmaceutically acceptable formulation (e.g., in a physiologically acceptable solvent, buffered to a physiological pH, etc.). The composition may be in a solution, a suspension, an emulsion, etc., and it may be administered in the form of eye drops, a cream, an ointment, a gel, an injectable, etc., to the eye and/or the eye lid. The composition contains rapamycin and/or ascomycin in an amount effective to treat an ocular condition without substantial toxicity. As one example, the composition may contain rapamycin in a formulation for topical administration in an amount ranging from about 1 ng rapamycin to about 10 μg rapamycin. As another example, the composition may contain ascomycin in a formulation for topical administration containing be formulated as a cream containing ascomycin in an amount ranging from about 1 ng ascomycin to about 10 μg ascomycin. In one embodiment, a patient may self-administer the composition at a prescribed dosing interval (e.g., once a day, twice a day, as needed, etc.). In another embodiment, a medical professional may administer an intraocular injection. Alternatively, the composition may be a lipid or another type of matrix containing milligram quantities of rapamycin and/or ascomycin. In this embodiment, the formulation is implanted in the eye and sustainedly releases the agent over an extended period of time.

These and other embodiments of the invention will be further appreciated with reference to the following detailed description.

DETAILED DESCRIPTION

Methods are disclosed to ameliorate ocular conditions in need of treatment by intraocularly administering compositions containing rapamycin, ascomycin, and/or combinations of rapamycin and ascomycin as an active component. Intraocular administration provides direct effects to the eye while avoiding problems associated with systemic administration. Rapamycin is also known as sirolimus, RAPA and Rapamune. It is a triene macrolide antibiotic derived from *Streptomyces hydroscopicus* and originally developed as an antifungal agent. Subsequently, it has shown anti-inflammatory, anti-tumor, and immunosuppressive properties. Ascomycin is also known as pimecrolimus, Immunomycin, and FR-900520. It is an ethyl analog of tacrolimus (FK506) and has strong immunosuppressant properties. It inhibits Th1 and Th2 cytokines, and preferentially inhibits activation of mast cells, and is used to treat contact dermatitis and other dermatological conditions. Rapamycin and ascomycin are commercially available, e.g., A.G. Scientific, Inc. (San Diego, Calif.).

Regarding its immunosuppressive potential, rapamycin has some synergetic effect with Cyclosporin A. It has been reported that rapamycin has a different mode of action compared to Cyclosporin A and tacrolimus, two other immunosuppresants. All three agents are immunosuppressants which affect the action of immune cell modulators (cytokines), but do not affect the immune cells themselves. However, while all three agents affect immune cell modulators, they do so differently: Cyclosporin A and tacrolimus prevent synthesis of cytokine messengers, specifically interleukin-2, while rapamycin acts on cytokine that has already been synthesized, preventing it from reaching immune cells.

Rapamycin inhibits inflammation by acting on both T-lymphocytes and dendritic cells. The latter are the first cells to recognize antigens. Rapamycin blocks the growth of dendritic cells and a number of other cells, such as tumors and endothelial cells, which are activated by the tumor cell releasing vascular endothelial growth factor (VEGF). VEGF is a central regulator of angiogenesis (formation of new blood vessels from pre-existing vessels) and vasculogenesis (development of embryonic vasculature through an influence on endothelial cell differentiation and organization). Diseases that are characterized by abnormal angiogenesis and vasculogenesis, such as some cancers and some ocular diseases, may show abnormal production of VEGF. Thus, control of VEGF function may be one means to control or treat these diseases. Rapamycin has also been used in the prevention of smooth muscle hyperplasia after coronary stent surgery.

Methods which include administering rapamycin or ascomycin, either alone or in combination, may be useful for alleviating the effects of conditions that result in lack of moisture or wetness in the eye. Two examples of pathological conditions resulting in dry eye include pemphigus and Sjögren's syndrome, which affect the eye by either damaging the conjunctival cells responsible for maintaining the wetness of the cornea and the conjunctiva, or by damaging the lacrimal glands of the eye and/or the meibomian glands of the eye lid. Other examples of pathological conditions resulting in dry eye include hypolacrimation, alacrima, xerophthalmia, Stevens-Johnson syndrome, pemphigus, ocular pemphigoid, marginal blepharitis, diabetes, and/or post-corneal surgery (including but not limited to post-LASIK surgery). Examples of non-pathological conditions resulting in dry eye include the aging process, environmental factors (e.g., dry home and/or work environments), and extended use of visual display terminals (e.g., employment, recreation).

The inventive method is also useful for patients with inflammation and in which generation of an immune response is implicated in ocular diseases or diseases having an ocular component. Examples include diabetic retinopathy, age-related macular degeneration, retinitis pigmentosa, and uveitis (anterior, intermediate, or posterior). In addition, inflammatory responses accompanying bacterial, fungal, and viral disease also affect the eye, and are amenable to methods of therapy using rapamycin.

Rapamycin alone, ascomycin alone, or a combination of rapamycin and ascomycin, may be intraocularly administered by any route. The agent(s) may be administered topically to the eye or eye lid, for example, using drops, an ointment, a cream, a gel, a suspension, etc. The agent(s) may be formulated with excipients such as methylcellulose, hydroxypropyl methylcellulose, hydroxypropyl cellulose, polyvinyl pyrrolidine, neutral poly(meth)acrylate esters, and other viscosity-enhancing agents. The agent(s) may be injected into the eye, for example, injection under the conjunctiva or tenon capsule, intravitreal injection, or retrobulbar injection. The agent(s) may be administered with a slow release drug delivery system, such as polymers, matrices, microcapsules, or other delivery systems formulated from, for example, glycolic acid, lactic acid, combinations of glycolic and lactic acid, liposomes, silicone, polyanhydride polyvinyl acetate alone or in combination with polyethylene glycol, etc. The delivery device can be implanted intraocularly, for example, implanted under the conjunctiva, implanted in the wall of the eye, sutured to the sclera, for long-term drug delivery.

Rapamycin alone, ascomycin alone, or a combination of rapamycin and ascomycin may be administered in a topical formulation for treatment of ocular conditions. In one embodiment, the agent(s) is formulated for topical administration to stimulate tear production by administering a composition containing rapamycin at a concentration in the range of about 50 pg/ml (0.000000005%) to about 50 µg/ml (0.005%), ascomycin at a concentration in the range of about 50 pg/ml to about 50 µg/ml, or a combination of rapamycin and ascomycin to achieve a total concentration of both agents of about 50 pg/ml to about 50 µg/ml. Within this range the agent(s) has wide safety and efficacy, permitting specific doses or administration protocols to be formulated for specific applications. For example, some patients may prefer once a day administration compared to administration more than once a day, so a higher concentration of agent(s) may be used for these patients.

In another embodiment, rapamycin in amounts ranging from about 1 ng to about 10 µg is contained in an aqueous-based cream excipient. In another embodiment, ascomycin in amounts ranging from about 1 ng to about 10 µg is contained in an aqueous-based cream excipient. In another embodiment, rapamycin and ascomycin are both present in an aqueous-based cream excipient in various proportions to achieve a total amount of combined agents of about 1 ng to about 10 µg. The drug(s) may be incorporated directly into the cream in solution, or may be contained in liposomes or microspheres either in solution or in an anhydrous form. The cream formulation is usually applied to the eye at bedtime, but it may be applied any time throughout the day if the cream does not cause blurred vision. In another embodiment, the agent(s) is formulated as a solution or suspension and is applied topically in the form of eye drops.

Rapamycin may also be administered by injection. Intraocular injection may be desirable or necessary, for example, for conditions in which topical administration is either not advised or is inadequate, for patients who have difficulty self-administering medications, etc. In one embodiment, the volume injected is less than 0.3 ml. In another embodiment, the volume injected is in the range of about 0.01 ml to about 0.3 ml. For intravitreal administration (injection into the vitreous), rapamycin concentrations in the range of about 1 ng/0.1 ml to about 200 µg/ml (0.02%) may be used without toxicity or adverse side effects. In a specific embodiment, a dose of about 50 µg/0.1 ml is administered. Injection may also be subconjunctival (into the subconjunctiva), or retrobulbar (behind the eyeball). For subconjunctival injection, a dose in the range of about 1 ng/ml to about 200 µg/ml may be used. For retrobulbar injection, a dose in the range of about 20 µg/ml to about 200 µg/mi may be used. Ascomycin may also be formulated as an injectable for intraocular injection. The same doses as used for intraocular injection of rapamycin are used for intraocular injection of ascomycin.

For long term delivery of rapamycin and ascyomycin, either alone or in combination, and/or for sustained release, a matrix housing or containing the agent(s) may be implanted into the eye. For example, a reservoir containing in the range of about 3 mg to about 5 mg of agent(s) is estimated to be able to release about 1 µg agent(s) per day. At such a release rate, continuous, sustained dosing may occur over 1000 to 5000 days. If less than 1 µg of agent(s) per day is released, sustained dosing may last up to or more than a decade. In one embodiment, less than 50 µg/day of agent(s) is released from the matrix. In another embodiment, agent(s) is release form the matrix at a rate in the range of about 50 pg/day to about 50 µg/day. In another embodiment, agent(s) is released from the matrix at a rate in the range of about 1 µg/day to about 5 µg/day.

A surgically implanted intraocular device or matrix may be a reservoir container having a diffusible wall of polyvinyl alcohol or polyvinyl acetate and containing milligram quantities of rapamycin, ascomycin, or a combination of rapamycin and ascomycin may be implanted in the sclera. As another example, milligram quantities of agent(s) may be incorporated into a polymeric matrix having dimensions of about 2 mm by 4 mm, and made of a polymer such as polycaprolactone, poly(glycolic) acid, poly(lactic) acid, or a polyanhydride, or a lipid such as sebacic acid, and may be implanted on the sclera or in the eye. This is usually accomplished with the patient receiving either a topical or local anesthetic and using a small (3–4 mm incision) made behind the cornea. The matrix, containing the agent(s), is then inserted through the incision and sutured to the sclera using 9–0 nylon.

Rapamycin alone, ascomycin alone, or a combination of rapamycin and ascomycin may also be contained within an inert matrix for either topical application or injection into the eye. As one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. The agent(s), in amounts ranging from nanogram to microgram quantities, is added to a solution of egg PC, and the lipophilic drug binds to the liposome.

A time-release drug delivery system may be implanted intraocularly to result in sustained release of the active agent(s) over a period of time. The implantable formation may be in the form of a capsule of any of the polymers previously disclosed (e.g., polycaprolactone, poly(glycolic) acid, poly(lactic) acid, polyanhydride) or lipids that may be formulation as microspheres. As an illustrative example, rapamycin may be mixed with polyvinyl alcohol (PVA), the mixture then dried and coated with ethylene vinyl acetate, then cooled again with PVA. Rapamycin bound with liposomes may be applied topically, either in the form of drops or as an aqueous based cream, or may be injected intraocularly. In a formulation for topical application, the drug is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the patient a constant exposure to the drug over time. In a time-release formulation, the microsphere, capsule, liposome, etc. may contain a concentration of rapamycin that could be toxic if administered as a bolus dose. The time-release administration, however, is formulated so that the concentration released at any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety.

As another example, rapamycin alone, ascomycin alone, or a combination of rapamycin and ascomycin may be dissolved in an organic solvent such as DMSO or alcohol as previously described and containing a polyanhydride, poly(glycolic) acid, poly(lactic) acid, or polycaprolactone polymer.

Rapamycin and/or ascomycin, either alone or in combination with immunosuppressant agents such as Cyclosporin A, tacrolimus, etc., may be administered intraocularly and without substantial toxicity, to treat ocular conditions associated with an autoimmune response and/or involving an antigen/antibody reaction. Exemplary diseases include retinopathy in diabetic patients, macular degeneration, retinitis pigmentosa, inflammatory diseases of the eye such as Behcet's syndrome, toxoplasmosis, Birdshot choroidopathy, histoplasmosis, pars planitis, sarcoidosis, inflammatory diseases of the choroid of unknown etiology such as sympathetic ophthalmia, serpiginous choroidopathy, diffuse pigment epitheliopathy, Vogt-Koyanagi syndrome, polyarteritis nodosa, juvenile rheumatic arthritis, other conditions of the eye including uveitis (inflammation of the uvea), scleritis, (inflammation of the sclera), neuritis (inflammation of the optic nerve), or papillitis (inflammation of the optic nerve head) using the methods and formulations previously described. This may be achieved by one or a combination of factors, such as by slowing disease progression, lessening its severity, lengthening the time of onset, etc.

The toxicity of rapamycin, which had been reported with rapamycin administered systemically, was thought to limit its intraocular use. Ocular toxicity may manifest as a gross and/or histologic retinal and/or vitreous toxic reaction. Evidence of such a toxic reaction may include one or more of white vitreous bodies, white vitreous opacities, electroretinography abnormalities such as reduction in mean B-wave amplitude in both scotopic and photopic conditions, occlusion of the temporal retinal vessels, and fibrin deposits.

In one embodiment, rapamycin alone, ascomycin alone, or a combination or rapamycin and ascomycin, is administered in an amount or at a dose that does not result in substantial toxicity to the eye. As used herein, a lack of substantial toxicity encompasses both the absence of any manifestations of toxicity, as well as manifestations of toxicity which one skilled in the art would consider not sufficiently detrimental to decrease or cease treatment. As one example, fibrin deposits may be present indicating some toxicity, but less than substantial toxicity if their duration, number, etc., as determined by one skilled in the art, does not warrant that treatment be stopped. As another example, white vitreous bodies and fibrin bodies may be present indicating some toxicity, but less than substantial toxicity if their duration, number, etc., as determined by one skilled in the art, does not warrant that treatment be stopped.

Intraocular administration of a dose up to about 200 μg of either rapamycin or ascomycin, or a combination of rapamycin and ascomycin to achieve a final dose of up to about 200 μg, does not result in substantial toxicity. This dose is similar to the dose of 250 μg tacrolimus for administration without substantial toxicity, reported in co-pending patent application Ser. No. 10/247,220, which is expressly incorporated by reference herein in its entirety. The intravenous solution form of rapamycin may be diluted to achieve the indicated concentration using 0.9% NaCl or 5% dextrose, or an organic solvent such as dimethylsulfoxide (DMSO) or alcohol, preferably a low molecular weight alcohol. Intraocular administration may be any of the routes and formulations previously described. For injection, either a solution, emulsion, suspension of a liquid, capsular formulation of microspheres or liposomes, etc. may be used.

To treat uveitis, rapamycin may be injected subconjunctivally at a dose in the range of about 1 ng/ml to about 200 μg/ml, or intravitreally at a dose of about 1 ng/0.1 ml to about 200 μg/ml. In one embodiment, the dose is about 50 μg/0.1 ml. To treat scleritis involving the anterior sclera, rapamycin may be administered topically. To treat scleritis involving the posterior sclera, rapamycin may be administered by retrobulbar injection at a dose in the range of about 20 μg/ml to about 200 μg/ml and dissolved in DMSO or a low concentration of alcohol. To treat neuritis or papillitis, rapamycin may be administered by retrobulbar injection at a dose in the range of about 20 μg/ml to about 200 μg/ml. Ascomycin may be administered by the same routes for the given indications using the same doses as for rapamycin.

Diabetic retinopathy is a leading cause of blindness. Patients with diabetes mellitus have an absolute or relative lack of circulating insulin and, through a variety of factors, frequently present with vascular changes in the retina. These changes manifest in retinal microaneurysms, small hemorrhages, and exudates, and lead to the formation of scar tissue. New blood vessels may form around the optic disk (proliferative retinopathy). Over time, the cumulative results of such vascular effects lead to ocular pathologies which, ultimately, decrease vision in the diabetic patient. Thus, compositions and methods which reduce these vascular changes, or reduce their effects, improve the chances of a diabetic patient either maintaining vision, or at least slowing loss of vision.

Macular degeneration, also called age related macular degeneration (AMD) is a pathological condition that results in proliferation of new blood vessels in the subretinal area. While the presence of the new vessels themselves is not problematic, new vessels leak blood and other serous fluid which accumulate in surrounding spaces. It is this fluid accumulation that leads to visual impairment. For example, in the retina, both the large vessels and the capillaries normally have intact vessel walls. In the choroid, the large vessels normally have intact vessel walls, but the capillary walls or membranes contain fenestrations or openings. Any endogenous or exogenous fluid present in these capillaries, for example, blood, serous fluid, solubilized drug, etc. will leak outside the vessels and into the surrounding area. The accumulation of fluid can result in serous and hemorrhagic detachment of the retinal pigment epithelium and neurosensory retina, and can lead to loss of vision due to fibrous deform scarring. Patients with an early stage of AMD can be diagnosed by the presence in the eye of abnormal clumps of pigments, termed drusen, which are dead outer segments of photoreceptor cells under the retinal pigment epithelium. The presence of large, soft drusen in the eye indicates a pre-stage of exudative AMD, and places these patients at higher-than-average risk for developing neovascularizations, especially if one eye is already affected.

Retinitis pigmentosa is a general term that encompasses a disparate group of disorders of rods and cones, which are the sensory structures in the retina. While retinitis pigmentosa is a genetic disorder, and is not an inflammatory process, one manifestation of the disease is the presence of irregular black deposits of clumped pigment in the peripheral retina. Thus, there is likely at least some immune component to retinitis pigmentosa which treatment with an immunosuppressant drug may help to alleviate.

A possible mechanism for the therapeutic efficacy of rapamycin and ascomycin in ocular disease involves their immunosuppressant activity. For example, diabetic patients treated with immunosuppressant drugs for reasons unrelated to vision develop less retinopathy over time than other diabetic patients. As another example, the drusen that is present in AMD constitutes a chronic inflammatory stimulus that becomes the target for encapsulation by a variety of inflammatory mediators, such as compliment. Treatment with immunosuppressant drug may ameliorate this reaction. Immunosuppressant therapy results in decreased numbers of circulating immunocompetent cells such as lymphocytes. These cells otherwise have the potential to participate in an immune response, to lodge within the small capillaries and arterioles of the eye to form blockages and hence occlude blood flow, etc. In addition to lymphocytes, other hematopoietic cells may also be affected by immunotherapy, and include erythrocytes (red blood cells), megakaryocytes (precursors to platelets) and thrombocytes (platelets), and other leukocytes (white blood cells), such as monocytes and granulocytes. Local or in situ administration of immunosuppressant agents to the eye would be expected to decrease the number of these cells, resulting in reduction in the immune response, less blockage, increased blood flow, and increased patency of the ocular vessels.

Rapamycin, ascomycin, or a combination of the two in any of the previously described formulations, dosages, compositions, routes of administration, etc. may be employed. The active ingredient may be rapamycin or ascomycin alone. In one embodiment, rapamycin may be administered as described in combination with one or more known immunosuppressant agents, such as Cyclosporin A and/or tacrolimus. In another embodiment, rapamycin may be administered as described in combination with one or more antibiotics. In another embodiment, ascomycin may be administered as described in combination with one or more known immunosuppressant agents. In another embodiment, ascomycin may be administered as described in combination with one or more antibiotics. Such a combination is useful for treating ocular diseases having a microbial component, for example, conjunctivitis. Antibiotics which may be used are known to one skilled in the art (see, for example, Goodman and Gilman's The Pharmacological Basis of Therapeutics, Eighth Edition, Gilman et al., Eds. (Pergamon Press, New York 1990, pages 1024–1033, which is incorporated by reference herein). Such exemplary antibiotics are not limiting, and the invention encompasses antibiotics presently known and unknown in combination with rapamycin and/or ascomycin for treatment of ocular disease. Because rapamycin is administered locally to the eye (e.g., intraocular injection, topical ocular application), the undesirable effects brought about by administration of systemic immunosuppressant therapy (e.g., decreased peripheral blood leukocyte count, susceptibility to infections, hepatic and renal toxicity of the immunosuppressant agent itself, etc.) are absent.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method to treat a posterior segment ocular condition selected from diabetic retinopathy, retinitis pigmentosa, or age related macular degeneration in a patient comprising intraocularly administering a composition comprising a drug selected from the group consisting of rapamycin, ascomycin, and combinations thereof, the drug at a concentration up to about 200 µg/ml in a pharmaceutically acceptable formulation effective to treat the diabetic retinopathy, retinitis pigmentosa, or age related macular degeneration condition without substantial toxicity wherein the composition is administered by at least one of intraocular injection.

2. The method of claim 1 wherein the composition further comprises Cyclosporin A, tacrolimus, or combinations thereof.

3. A method to treat a posterior segment ocular condition selected from diabetic retinopathy, retinitis pigmentosa, or age related macular degeneration in a patient comprising intraocularly administering a composition consisting essentially of rapamycin in a pharmaceutically acceptable formulation effective to treat the diabetic retinopathy, retinitis pigmentosa, or age related macular degeneration condition by a method selected from the group consisting of topical administration at a concentration of about 50 pg/ml to less than 1 µg/ml, subconjunctival injection at a dose in the range of about 1 ng/ml to about 200 µg/ml, intravitreal injection at a dose in the range of about 1 ng/0.1 ml to about 200 µg/ml, or retrobulbar injection at a dose in the range of about 20 µg/ml to about 200 µg/ml.

4. The method of claim 3 wherein injection is intravitreal at a dose of about 50 µg/0.1 ml.

5. An ocular treatment method comprising intraocularly administering to a patient after corneal surgery a composition consisting essentially of rapamycin in a pharmaceutically acceptable formulation and in an amount effective to enhance post-surgical ocular moisture in the patient wherein the composition is administered at a concentration up to about 200 µg/ml by at least one of intraocular injection, or the composition is administered topically at a concentration in the range between about 50 pg/ml to less than 1 µg/ml.

6. The method of claim 5 wherein the composition is administered by subconjunctival injection at a dose in the range of about 1 ng/ml to about 200 µg/ml, intravitreal injection at a dose in the range of about 1 ng/0.1 ml to about 200 µg/ml, or retrobulbar injection at a dose in the range of about 20 µg/ml to about 200 µg/ml.

7. An ocular treatment method comprising intraocularly administering to a patient after corneal surgery a composition consisting essentially of ascomycin in a pharmaceutically acceptable formulation and in an amount effective to enhance post-surgical ocular moisture in the patient wherein the composition is administered at a concentration up to about 200 µg/ml by at least one of intraocular injection, or the composition is administered topically at a concentration in the range between about 50 pg/ml to less than 1 µg/ml.

8. The method of claim 7 wherein the composition is administered by subconjunctival injection at a dose in the range of about 1 ng/ml to about 200 µg/ml, intravitreal injection at a dose in the range of about 1 ng/0.1 ml to about 200 µg/ml, or retrobulbar injection at a dose in the range of about 20 µg/ml to about 200 µg/ml.

9. A method to treat an ocular condition in a patient comprising intraocularly administering to the patient a pharmaceutically acceptable formulation of a drug selected from the group consisting of rapamycin, ascomycin, and combinations thereof, in an amount up to about 200 µg/ml effective to treat an ocular condition selected from diabetic retinopathy, retinitis pigmentosa, or age related macular degeneration without substantial toxicity and at least one antibiotic, wherein the composition is administered by at least one of intraocular injection at a concentration up to about 200 µg/ml, or the composition is administered topically at a concentration in the range between about 50 pg/ml to less than 1 µg/ml.

10. A method to treat an ocular posterior segment condition selected from diabetic retinopathy, retinitis pigmentosa, or age related macular degeneration in a patient comprising intraocularly administering a composition consisting essentially of ascomycin in a pharmaceutically acceptable formulation effective to treat the diabetic retinopathy, retinitis pigmentosa, or age related macular degeneration condition by a method selected from the group consisting of topical administration at a concentration between about 50 pg/ml to less than 1 µg/ml, subconjunctival injection at a dose in the range of about 1 ng/ml to about 200 µg/ml, intravitreal injection at a dose in the range of about 1 ng/0.1 ml to about 200 µg/ml, or retrobulbar injection at a dose in the range of about 20 µg/ml to about 200 µg/ml.

11. The method of claim 10 wherein injection is intravitreal at a dose of about 50 µg/0.1 ml.

* * * * *

UNITED STATES PATENT AND TRADEMARK OFFICE
CERTIFICATE OF CORRECTION

PATENT NO. : 7,083,802 B2  Page 1 of 1
APPLICATION NO. : 10/631143
DATED : August 1, 2006
INVENTOR(S) : Gholam Peyman It is certified that error appears in the above-identified patent and that said Letters Patent is hereby corrected as shown below:

In The Claims:

| | |
|---|---|
| Column 10, Claim 1, line 11 | "or" should be --and-- |
| Column 10, Claim 1, line 20 | delete "at least one of" |
| Column 10, Claim 3, line 25 | "or" should be --and-- |
| Column 10, Claim 3, line 36 | "or" should be --and-- |
| Column 10, Claim 5, line 46 | delete "at least one of" |
| Column 10, Claim 7, line 61 | delete "at least one of" |
| Column 11, Claim 9, line 9 | "pigimentosa, or" should b --pigmentosa, and-- |
| Column 11, Claim 9, line 11 | delete "at least one of" |
| Column 12, Claim 10, line 1 | "or" should be --and-- |
| Column 12, Claim 10, line 11 | "or" should be --and-- |

Signed and Sealed this

Twenty-eighth Day of November, 2006

JON W. DUDAS
*Director of the United States Patent and Trademark Office*